(12) United States Patent
Prevost et al.

(10) Patent No.: US 10,954,176 B2
(45) Date of Patent: Mar. 23, 2021

(54) PROCESS FOR PRODUCING PARA-XYLENE USING A STEP IN A SIMULATED MOVING BED AND A STEP OF FRACTIONATION VIA A THREE-FRACTION COLUMN

(71) Applicant: AXENS, Rueil-Malmaison (FR)

(72) Inventors: Isabelle Prevost, Rueil-Malmaison (FR); Jerome Pigourier, Rueil-Malmaison (FR); Pierre-Yves Martin, Rueil-Malmaison (FR); Arnaud Cotte, Rueil-Malmaison (FR)

(73) Assignee: AXENS, Rueil-Malmaison (FR)

( * ) Notice: Subject to any disclaimer, the term of this patent is extended or adjusted under 35 U.S.C. 154(b) by 0 days.

(21) Appl. No.: 16/454,406

(22) Filed: Jun. 27, 2019

(65) Prior Publication Data

US 2020/0002252 A1     Jan. 2, 2020

(30) Foreign Application Priority Data

Jun. 29, 2018    (FR) ...................................... 1856050

(51) Int. Cl.
     *B01D 3/14*        (2006.01)
     *C07C 7/04*         (2006.01)
     *C07C 15/08*       (2006.01)
     *B01D 3/32*        (2006.01)

(52) U.S. Cl.
CPC .............. *C07C 15/08* (2013.01); *B01D 3/141* (2013.01); *B01D 3/145* (2013.01); *C07C 7/04* (2013.01); *B01D 3/322* (2013.01)

(58) Field of Classification Search
None
See application file for complete search history.

(56) References Cited

U.S. PATENT DOCUMENTS

| | | | |
|---|---|---|---|
| 7,915,471 B2 | 3/2011 | Leflaive et al. | |
| 8,802,914 B2 | 8/2014 | Corradi | |
| 10,059,644 B2 | 8/2018 | Tinger et al. | |
| 2014/0179975 A1 | 6/2014 | Banerjee et al. | |
| 2016/0318827 A1* | 11/2016 | Tinger | ................... B01D 3/143 |
| 2017/0210682 A1* | 7/2017 | Dreux | ................... C07C 5/2737 |

FOREIGN PATENT DOCUMENTS

| | | | | |
|---|---|---|---|---|
| FR | 2862638 B1 | 12/2005 | | |
| WO | 13089902 A1 | 6/2013 | | |
| WO | WO-2016008652 A1 * | 1/2016 | ........... | C07C 5/2775 |
| WO | 16175898 A1 | 11/2016 | | |

OTHER PUBLICATIONS

Search report of corresponding FR1856050 dated Mar. 15, 2019 (pp. 1-2).

* cited by examiner

*Primary Examiner* — In Suk C Bullock
*Assistant Examiner* — Alyssa L Cepluch
(74) *Attorney, Agent, or Firm* — Millen White Zelano and Branigan, PC

(57) ABSTRACT

The present invention relates to a process for producing high-purity para-xylene, comprising a single step of separation by adsorption in an SMB, with a subsequent step of separation by distillation in a first three-fraction distillation column producing at least two raffinates and optionally of two isomerization steps, making it possible to improve the overall para-xylene yield of the aromatic loop and to minimize the economic impact.

13 Claims, 4 Drawing Sheets

PROCESS FOR PRODUCING PARA-XYLENE USING A STEP IN A SIMULATED MOVING BED AND A STEP OF FRACTIONATION VIA A THREE-FRACTION COLUMN

TECHNICAL FIELD para-Xylene is mainly used for the production of terephthalic acid and of polyethylene terephthalate resins, for producing synthetic textiles, bottles, and more generally plastics.

The present invention relates to a process for producing high-purity para-xylene using a specific sequence of steps for achieving high production of para-xylene.

PRIOR ART

The production of high-purity para-xylene using a step of separation by adsorption is well known in the prior art. Industrially, said step is performed within a sequence of "C8-aromatic loop" or "xylene loop" processes. This "C8-aromatic loop" includes a step of removing heavy compounds (i.e. compounds containing more than 9 carbon atoms, denoted C9+) in a distillation column known as a "xylenes column".

The head stream from this column, which contains the C8-aromatic isomers, is then sent into the para-xylene separation process, which is generally a step of separation by adsorption in a simulated moving bed.

The extract obtained on conclusion of the step of separation by adsorption in a simulated moving bed, which contains para-xylene, is then distilled using an extraction column and then a toluene column, to obtain high-purity para-xylene.

The raffinate obtained on conclusion of the step of separation by adsorption in a simulated moving bed, which is rich in meta-xylene, ortho-xylene and ethylbenzene, after a step of removing the desorbent by distillation, is used in an isomerization step, making it possible to obtain a mixture in which the proportion of xylenes (or ortho-, meta- and para-xylenes) is virtually at thermodynamic equilibrium, and depleted in ethylbenzene. This mixture is again sent into the "xylenes column" with the fresh feedstock for the production of para-xylene.

The prior art proposes numerous variants of this scheme using one or more separation steps (by adsorption, crystallization, distillation or by membrane) and/or one or more gas-phase isomerization steps (converting the ethylbenzene by isomerization into xylenes or by dealkylation into benzene), or liquid-phase isomerization steps (not converting the ethylbenzene).

One of the variations proposed in the prior art consists in performing the isomerization in two separate steps. The first step makes it possible to isomerize the ethylbenzene contained in the raffinate rich in meta-xylene, ortho-xylene and ethylbenzene. The effluent from this first isomerization section, which is depleted in ethylbenzene, is sent after fractionation into a second section comprising the separation of the para-xylene by adsorption followed by a second step of isomerization of the xylenes to para-xylene.

Optimization of the isomerization catalysts and of the operating conditions makes it possible to limit the undesirable side reactions. Thus, it is established that, in order to promote the conversion of ethylbenzene into xylenes, it is preferable to perform the isomerization in the vapour phase at high temperature. It is likewise known that isomerization in the liquid phase at low temperature minimizes the spurious cracking transalkylation and dismutation reactions, and also limits the conversion of ethylbenzene.

Processes for producing high-purity para-xylene using two isomerization steps are more complex and lead to limited gains in para-xylene production. The reason for this is that, to achieve sufficiently high degrees of ethylbenzene conversion, the operating conditions of the first gas-phase isomerization step are harsh and are accompanied by side reactions that lead to losses of C8 aromatics, which has a substantial impact on the overall yield of para-xylene.

Patent FR 2862638 describes a process for producing para-xylene from a hydrocarbon feedstock, using two simulated moving bed separation steps and two isomerization steps. The drawback of this process is that it requires two simulated moving bed separation steps, which entails a substantial increase in the production cost.

Patents FR 3023840 and FR 3023841 describe alternative processes comprising two simulated moving bed separation steps and isomerization unit steps in which the two isomerization steps are performed in series or in parallel on the circuit of the raffinate from the first simulated moving bed separation unit.

Patent FR 3023842 describes an alternative process comprising a step of simulated moving bed adsorption and two steps of isomerization, on the one hand in the gas phase and on the other hand in the liquid phase, in which the two isomerization units are fed with the same feedstock derived from the fractionation of the effluent from the adsorption unit.

In the field of the invention, a person skilled in the art is constantly seeking to limit the investment costs and the operating costs for running the xylene loop used, while at the same time increasing the amount of high-purity para-xylene obtained.

Surprisingly, the Applicant has discovered that the combination, in a process for producing high-purity para-xylene, of a step of separation by adsorption in an SMB, with a subsequent step of separation by distillation in a first three-fraction distillation column producing at least two raffinates and of two isomerization steps, makes it possible to improve the overall para-xylene yield of the aromatic loop and to minimize the economic impact.

An advantage of the process according to the present invention is that it achieves a high production of para-xylene, with small trade-offs in terms of capacity increase, in contrast with the prior art processes.

Another advantage of the invention is that it has great flexibility, which can be exploited in operation, thus making it possible to adapt to the changes in catalytic performance for each isomerization step implemented.

DEFINITIONS & ABBREVIATIONS

Throughout the description, the terms or abbreviations below have the following meaning.

It is pointed out that, throughout this description, the expression "between . . . and . . . " should be understood as including the mentioned limits.

The abbreviation EB denotes ethylbenzene.
The abbreviation PX denotes para-xylene.
The abbreviation OX denotes ortho-xylene.
The abbreviation MX denotes meta-xylene.
The term "xylenes" (also denoted XYL) refers to a mixture of at least two xylene isomers chosen from ortho-xylene, meta-xylene and para-xylene.
The abbreviation SMB denotes a simulated moving bed.

The term "C9+ hydrocarbons" refers to hydrocarbons containing at least 9 carbon atoms.

The term "C8+ hydrocarbons" refers to hydrocarbons containing at least 8 carbon atoms.

The term "C8 Aromatics", also denoted C8A, denotes aromatic hydrocarbons consisting of 8 carbon atoms, i.e. EB, PX, OX, MX and preferably EEB, OX, MX.

The term "raffinate" refers to a C8A mixture depleted in PX, and which may contain desorbent, i.e. which has a mass content of PX of less than 2.0%, preferably less than 1.5% and preferably of 1.0%.

For the purposes of the present invention, the term "free of" refers to a mass content of a given compound relative to the total mass of the fraction under consideration, for example of EB, of less than 0.5% by weight, preferably less than 0.1% and preferably less than 0.01%.

The term "residual amount" of a given compound refers to an amount whose mass content relative to the total mass of the fraction under consideration is less than 5.0% by weight, preferably between 5.0 and 1.0, preferably between 4.0 and 1.0, and preferably between 3.0 and 1.0% by weight.

In the present invention, the terms "effluents", "raffinates", "streams" and "fractions" are employed equivalently.

The term "two-fraction and three-fraction distillation column" refers to a distillation column for obtaining two and three fractions, respectively.

BRIEF DESCRIPTION OF THE INVENTION

The present invention thus relates to a process for producing para-xylene from a feedstock containing xylenes, ethylbenzene and C9+ hydrocarbons, comprising
a single step A of separation in a simulated moving bed of said feedstock performed with a zeolite as adsorbent and a desorbent, at a temperature of between 20 and 250° C., at a pressure of between 1.0 and 2.2 MPa, and with a volume ratio of the desorbent to the feedstock in the simulated moving bed separation unit of between 0.4 and 2.5;
said step A allowing the production of
a first fraction A1 containing a mixture of para-xylene and of desorbent, and
at least one second fraction A2 containing ethylbenzene (EB), ortho-xylene (OX) and meta-xylene (MX) and desorbent,
a step B of fractionation by distillation in at least one first distillation column B_C3 of said second fraction derived from step A, allowing the production of three fractions:
a first fraction B2 containing EB, OX and MX,
a second fraction B3 containing OX and MX, and
a third fraction B42 containing desorbent.

Preferably, the first fraction B2 derived from step B has an EB content greater than the EB content of the second fraction B3 derived from the first column B_C3 used in step B.

Preferably, the EB content of the first fraction is at least 1.0% greater than that of the second fraction.

Preferably, the distillation column used in step B comprises between 30 and 80 theoretical plates.

In another particular embodiment, the separation step A also allows the production of a third fraction A22 depleted in EB, containing a mixture of MX, OX and desorbent, said fractions A2 and A22 being sent into said fractionation step B.

Advantageously, in this embodiment, the third fraction A22 derived from step A is engaged in a second distillation column B-C4 allowing the production of a fraction B31 free of desorbent, containing MX and OX, and a fraction B43 consisting of desorbent.

In another particular embodiment, the second fraction B3 is engaged in the fractionation step B in a second distillation column B-C4, allowing the production of a fraction B31 free of desorbent, containing MX and OX, and a fraction B43 consisting of desorbent.

Advantageously, in this embodiment, the third fraction A22 derived from step A is introduced into the second distillation column B-C4 below the lateral point of injection of the second fraction B3 derived from the first distillation column B-C3.

Advantageously, the distillation step B uses a column comprising an internal wall.

Advantageously, the process also comprises a step C of vapour-phase isomerization of the first fraction B2 derived from a fractionation step containing EB, OX and MX.

Advantageously, the process also comprises a step D of liquid-phase isomerization of the second fraction B3 containing OX and MX derived from the first distillation column B_C3 used in the fractionation step B.

Advantageously, the process also comprises a step D of liquid-phase isomerization of the fraction B31 containing OX and MX derived from the second distillation column B_C4 used in the fractionation step.

Advantageously, the vapour-phase isomerization step C is performed at a temperature above 300° C., a pressure of less than 4.0 MPa, a space velocity of less than 10.0 h$^{-1}$, a mole ratio of hydrogen to hydrocarbon of less than 10.0, and in the presence of a catalyst including at least one zeolite having channels whose aperture is defined by a ring of 10 or 12 oxygen atoms (10 MR or 12 MR), and at least one metal from group VIII in a content of between 0.1% and 0.3% by weight.

Advantageously, the catalyst used in step C comprises from 1% to 70% by weight of a zeolite of EUO structural type, said zeolite comprising silicon and at least one element T preferably chosen from aluminium and boron, the Si/T ratio of which is between 5 and 100.

Advantageously, the liquid-phase isomerization step D is performed at a temperature of less than 300° C., a pressure of less than 4.0 MPa, a space velocity of less than 5.0 h$^{-1}$ and preferably between 2.0 and 4.0 h$^{-1}$, and in the presence of a catalyst including at least one zeolite having channels whose aperture is defined by a ring of 10 or 12 oxygen atoms (10 MR or 12 MR); preferably, said zeolite is of ZSM-5 type.

BRIEF PRESENTATION OF THE FIGURES

DETAILED DESCRIPTION OF THE INVENTION

Figure 1:
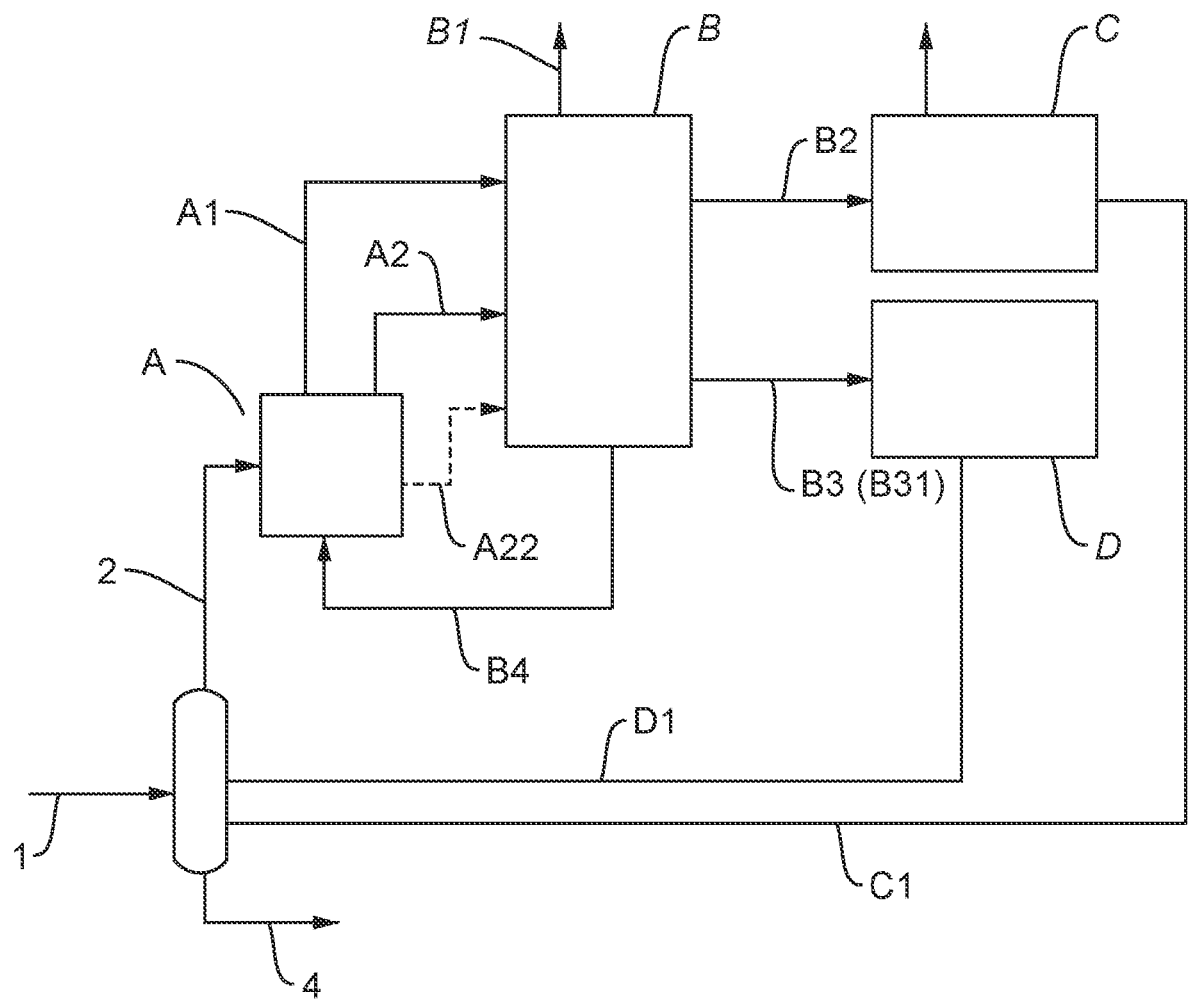
FIG. 1 is a general scheme of a xylene loop involving a step of separation by adsorption, a fractionation step, a vapour-phase isomerization step C and a liquid-phase isomerization step D.

The characteristics and advantages of the process according to the invention will become apparent on reading the description below of nonlimiting implementational examples, with reference to the numbering of the embodiments illustrated in the figures according to the invention.

For the purposes of the present invention, the various embodiments presented may be used alone or in combination with each other, without any limit to the combinations.

The present invention thus relates to a process for producing para-xylene from a feedstock containing xylenes, ethylbenzene and C9+ hydrocarbons, comprising
  a single step A of separation in a simulated moving bed of said feedstock performed with a zeolite as adsorbent and a desorbent, at a temperature of between 20 and 250° C., at a pressure of between 1.0 and 2.2 MPa, and with a volume ratio of the desorbent to the feedstock in the simulated moving bed separation unit of between 0.4 and 2.5;
  said step A allowing the production of
    a first fraction A1 containing a mixture of para-xylene and of desorbent, and
    at least one second fraction A2 containing ethylbenzene (EB), ortho-xylene (OX) and meta-xylene (MX) and desorbent,
  a step B of fractionation by distillation in at least one first distillation column B_C3 of said second fraction derived from step A, allowing the production of three fractions:
    a first fraction B2 containing EB, OX and MX,
    a second fraction B3 containing OX and MX, and
    a third fraction B42 containing desorbent.

The process according to the invention thus makes it possible to obtain, on conclusion of the fractionation step, two fractions having different proportions of C8A and thus to increase the PX proportion of the xylene isomerization performed with the catalyst operating in liquid phase and makes it possible to limit the losses of C8A.

Step A of Simulated Moving Bed Separation

According to the invention, the process comprises a single step A of separation in a simulated moving bed (SMB) of a feedstock containing xylenes, ethylbenzene and C9+ hydrocarbons. Said SMB separation step is performed with a zeolite as adsorbent and a desorbent and allowing the production of at least two fractions, a fraction A1 also known as the "extract" containing a mixture of para-xylene (PX) and of desorbent, a fraction A2 also known as the "raffinate" containing ethylbenzene (EB), ortho-xylene (OX), meta-xylene (MX) and desorbent.

The separation step is performed in a unit operating as a simulated moving bed in at least one separation column containing a plurality of interconnected beds and circulating desorbent in a closed loop, from which are derived two fractions:
  the first is an extract A1 comprising, preferably consisting of, para-xylene and desorbent such that, after fractionation to remove the desorbent, the PX reaches a commercial purity of 99.0% minimum and preferentially 99.9% by weight. Advantageously, the extract A1 represents at least 30% by weight of the total mass of the extract.
  the second fraction is a raffinate A2 which contains ethylbenzene (EB), meta-xylene, ortho-xylene and desorbent. Preferably, the raffinate is depleted in para-xylene, i.e. the mass content of PX in said raffinate is less than 1.0% and preferably less than 0.5%.

In another embodiment, at least three fractions are obtained in the single SMB separation step,
  the first is an extract A1 comprising, preferably consisting of, para-xylene and desorbent; after fractionation of this raffinate, the PX is obtained at the commercial specifications. Advantageously, the extract A1 represents at least 30% by weight of the total mass of the extract.
  two fractions A2 and A22 depleted in para-xylene, which contain variable proportions of a mixture of EB, MX, OX and desorbent.

In this embodiment, fractions A2 and the A22 have different proportions of EB, MX and OX, such that the EB content of the CA8 fraction of fraction A2 is greater than the EB content of the CA8 fraction of fraction A22. Preferably, fraction A2 depleted in PX contains a mixture of EB, MX, OX and desorbent; preferably, the EB is in a residual amount. Preferably, fraction A22 depleted in EB and PX contains a mixture of MX, OX and desorbent.

Preferably, the adsorbent used in the simulated moving bed separation unit is a barium-exchanged zeolite X or a potassium-exchanged zeolite Y or a barium- and potassium-exchanged zeolite Y.

In one embodiment, the desorbent contained in the feedstock treated via the process according to the invention is said to be heavy, i.e. it has a boiling point higher than that of the xylenes.

In another embodiment, the desorbent contained in the feedstock treated via the process according to the invention is said to be light, i.e. it has a boiling point lower than that of the xylenes.

Preferably, the desorbent used in the simulated moving bed separation unit is chosen from para-diethylbenzene, toluene, para-difluorobenzene or diethylbenzenes, alone or as a mixture.

Preferably, the volume ratio of the desorbent to the feedstock in the simulated moving bed separation unit is between 0.4 and 2.5 and preferably between 0.5 and 1.5.

Preferably, the simulated moving bed separation step A is performed at a temperature of between 20° C. and 250° C., preferably between 90° C. and 210° C. and even more preferably between 160° C. and 200° C., and at a pressure of between 1.0 and 2.2 MPa and preferably between 1.2 and 2.0 MPa.

Preferably, the adsorbent contains a plurality of interconnected beds spread over several zones delimited by the injections of the feedstock and of the desorbent, and also of the withdrawals of the extract, and of the raffinate(s). Depending on the number of raffinates, the adsorber will preferentially contain 15 to 18 beds.

According to a particular embodiment, the total number of beds in the separation unit (SMB) is between 10 and 30 beds, preferably between 15 and 18 beds spread over one or more adsorbers, the number of beds being adjusted so that each bed has a height of between 0.70 m and 1.40 m.

According to a particular embodiment (ALT 0, ALT 1), the distribution of the amount of adsorbent solid in each zone of the separation unit (SMB) is as follows:
  the amount of adsorbent solid in zone 1 is 17%±5%,
  the amount of adsorbent solid in zone 2 is 42%±5%,
  the amount of adsorbent solid in zone 3 is 25%±5%,
  the amount of adsorbent solid in zone 4 is 17%±5%.

According to a particular embodiment (ALT 2), the distribution of the amount of adsorbent solid in each zone of the separation unit (SMB) is as follows:
the amount of adsorbent solid in zone 1 is 18%±8%,
the amount of adsorbent solid in zone 2 is 41%±8%,
the amount of adsorbent solid in zone 3A is 18%±8%,
the amount of adsorbent solid in zone 3B is 14%±8%,
the amount of adsorbent solid in zone 4 is 9%±8%.

Fractionation Step B

The process according to the invention comprises a step B of fractionation by distillation in at least one first three-fraction column of fraction A2 containing ethylbenzene, ortho-xylene, meta-xylene and desorbent obtained from the separation step A. Said step B allows the production of
a first fraction B2 containing, preferably consisting of, EB, OX and MX, and
a second fraction B3 containing OX, MX and EB, preferably consisting of OX and MX and a residual amount of EB, and
a fraction B42 containing, preferably consisting of, desorbent.

Advantageously, the first fraction B2 and the second fraction B3 contain a mixture of EB, MX and OX in variable proportions such that the EB content in the C8A of the first fraction is greater than that of the second fraction. Preferably, the difference in EB content between the first and the second fractions is greater than 1.0%, preferably greater than 2.0%, preferably greater than 2.5%, preferably greater than 3.0% and preferably greater than 3.5%.

Advantageously, the three-fraction column used in step B has a number of theoretical plates of between 30 and 80, preferably between 35 and 75, preferably 40 and 80, very preferably between 45 and 65.

In one embodiment, when the second fraction B3 contains desorbent, said fraction is engaged in the fractionation step B in a second distillation column B-C4, allowing the production of a fraction B31 free of desorbent, containing MX and OX, and a fraction B43 consisting of desorbent.

Advantageously, when the fractionation of the raffinate is performed in a single three-fraction column containing 60 theoretical plates (implementation ALT0):
The position of the feed is located on plates 30 to 40 numbered from the condenser, and preferentially on plate 37.
The position of the withdrawal is located at least 10 to 25 plates above the feed and preferably 18 plates above the feed.

Advantageously, when the fractionation of the raffinate is performed in a first three-fraction column followed by a second two-fraction column, each preferably containing 47 theoretical plates (implementation ALT1, ALT2):
The position of the feed is located on plates 16 to 24 numbered from the condenser, and preferentially between plates 18 to 22.
The position of the withdrawal from the three-fraction column is located between 5 and 10 plates below the feed position and preferably between 7 and 8 plates below the feed.
The positions of the withdrawals and of the feeds for the raffinate columns may be adjusted homothetically as a function of the total number of plates installed in each of the raffinate columns.

Preferably, fraction A1 obtained from step A containing, and preferably consisting of, a mixture of PX and of desorbent is engaged in a step of fractionation by distillation in a distillation column (B-C1) allowing the production of a fraction B1 consisting of PX and a fraction B41 consisting of desorbent. Said distillation is performed according to the knowledge of a person skilled in the art.

In a particular embodiment of the invention (FIG. 2b, ALT0), fraction A2 obtained from step A is engaged in a step of fractionation by distillation in a first three-fraction distillation column B-C3 allowing the production at the top of a fraction B2 containing EB, MX and OX, as a side withdrawal a fraction B3 free of desorbent and containing OX and MX, preferably consisting of MX and OX and of a residual amount of EB, and at the bottom a fraction B42 comprising, preferably consisting of, desorbent.

In a preferred embodiment (FIG. 2c, ALT 1), said three-fraction column B-C3 is used so as to obtain
at the top a first fraction B2 containing, preferably consisting of, EB, OX and MX,
as a side withdrawal a second fraction B3 containing OX, MX, desorbent and a residual amount of EB, preferably consisting of OX, MX and desorbent, and
at the bottom a fraction B42 containing, preferably consisting of, desorbent.

Said fraction B3 is engaged in a second two-fraction distillation column B-C4 allowing the production of a fraction B31 free of desorbent, containing MX and OX, and a fraction B43 consisting of desorbent.

Advantageously, the embodiment ALT1 (FIG. 2c) makes it possible to reduce the xylene content in the EB-enriched fraction B2.

Figure 3A:
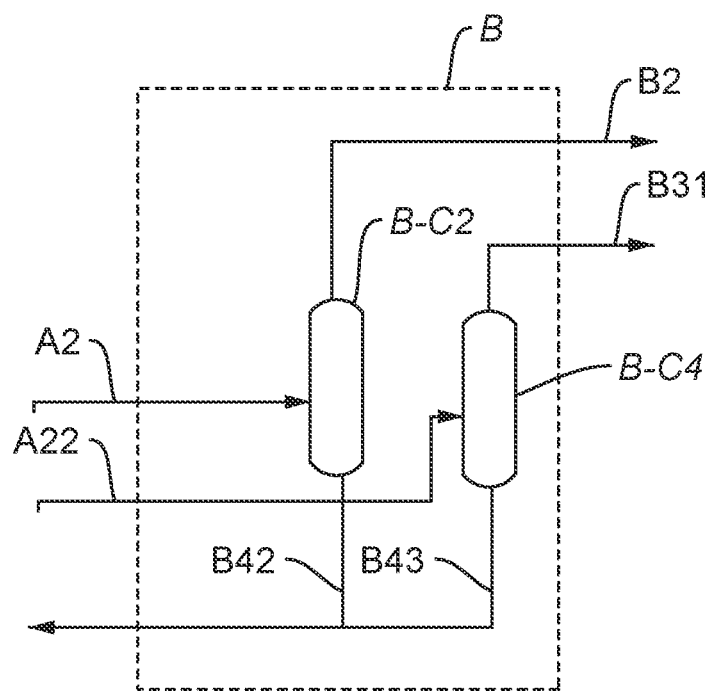
FIG. 3a represents step B of distillation of two raffinates obtained from step A according to the prior art.
Figure 3B:
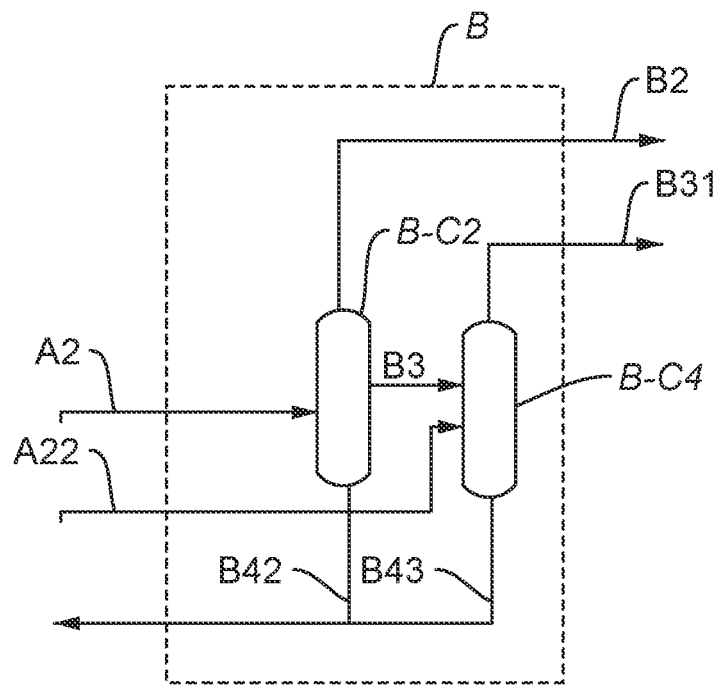
FIG. 3b is a variant, according to the invention, of step B of distillation of two raffinates obtained from step A.

In another preferred embodiment ALT2, step A allows the production of two fractions A2 and A22 (FIG. 3b, ALT 2). Said fraction A2 is engaged in the fractionation step B by distillation in a first three-fraction distillation column B-C3 allowing the production
at the top, of a first fraction B2 containing, preferably consisting of, EB, OX and MX,
as a side withdrawal, of a second fraction B3 containing OX, MX, desorbent and optionally a residual amount of EB, preferably consisting of OX, MX and desorbent, and
at the bottom, of a third fraction B42 containing, preferably consisting of, desorbent.

In the embodiment ALT2, said second fraction B3 obtained from the first column used in step B and fraction A22 obtained from step A are engaged in a second distillation column B-C4 allowing the production of a fraction B31 containing MX, OX, and optionally a residual amount of EB, preferably consisting of OX and MX, and a fraction B43 comprising, preferably consisting of, desorbent.

Preferably, fraction A22 is introduced into the second column, preferably a two-fraction column, of raffinate B-C4, below the point of injection of fraction B3.

Advantageously, in said embodiment ALT2 (FIG. 3b), the three-fraction column B-C3 receives only the EB-enriched fraction A2 of the raffinate A2, obtained from step A of separation by SMB, which makes it possible to further reduce the xylene content in the EB-enriched fraction B2 relative to the embodiment ALT1.

Advantageously, the desorbent fractions B41, B42 and B43 free of C8A are recovered at the bottom of each distillation column, combined as a fraction B4 and sent into the simulated moving bed adsorption step A.

When the desorbent of said step A is a compound heavier than xylenes, i.e. a compound with a higher boiling point than that of xylenes, the EB-enriched raffinate is produced at the top of the three-fraction column, the xylene-enriched raffinate is obtained in the side withdrawal, or alternatively at the top of the second distillation column.

When the desorbent of said separation step is a compound lighter than xylenes, i.e. a compound with a lower boiling point than that of xylenes, the xylene-enriched stream is produced at the bottom of the three-fraction column, the EB-enriched raffinate is obtained in the side withdrawal, or alternatively at the bottom of the second distillation column, the desorbent free of C8A is withdrawn at the top of the two columns and recycled into the adsorption step.

Advantageously the distillation columns B-C1, B-C3 and B-C4 used in the fractionation step B are operated at atmospheric pressure, the reboiling temperature is between 210 and 250° C., preferably between 220 and 240° C. and is preferably 230° C., and the reflux ratios expressed as reflux/feedstock mass ratio are between 1.0 and 3.0 and preferentially between 1.4 and 2.0.

Advantageously, the raffinate B3 recovered at the top of column B-C3 is obtained in the form of a liquid distillate withdrawn four plates under the condenser, said condenser is at total reflux and comprises a decantation sump to withdraw liquid water.

More precisely, when step B uses a distillation column (B-C3), the performance of the step of fractionation of the raffinate obtained by distillation (ALT0 and ALT1) is characterized by:
the degree of recovery (DR) of EB in the EB-enriched raffinate B2: $DR(EB)=EB_{(raffinate\ B2)}/(EB_{(raffinate\ B2)}+EB_{(raffinate\ B3)})$
the degree of recovery (DR) of the xylenes in the EB-enriched raffinate B2: $DR(XYL)=XYL_{(raffinate\ B2)}/(XYL_{(raffinate\ B2)}+XYL_{(raffinate\ B3)})$ When step B uses a second distillation column (B-C4), the performance of the step of fractionation of the raffinate obtained by distillation (ALT2) is characterized by:
the degree of recovery (DR) of EB in the EB-enriched raffinate B2: $DR(EB)=EB_{(raffinate\ B2)}/(EB_{(raffinate\ B2)}+EB_{(raffinate\ B31)})$
the degree of recovery (DR) of the xylenes in the EB-enriched raffinate B2: $DR(XYL)=XYL_{(raffinate\ B2)}/(XYL_{(raffinate\ B2)}+XYL_{(raffinate\ B31)})$ Advantageously, in the process according to the invention, the degree of recovery of ethylbenzene (denoted DR(EB)), is between 50% and 90%, and preferably between 80% and 90%.

Advantageously, in the process according to the invention, ALT 0 or ALT 1, when fractions A1 and A2 are engaged in the fractionation steps, the degree of recovery of the xylenes DR(XYL) has a difference of at least 2% less, preferably of at least 5%, preferably of at least 10% and preferably of at least 15% relative to the degree of recovery of ethylbenzene (DR(EB)).

Advantageously, when fractions A1, A2 and A22 are engaged in the fractionation steps, the degree of recovery of the xylenes DR(XYL) shows a difference at least strictly 20% less, preferably at least 23%.

According to another embodiment, the distillation step may be performed with any other distillation arrangement including a first three-fraction distillation column B-C3. Preferably, said three-fraction distillation column B-C3 of variants ALT0, ALT1 or ALT2 according to the invention comprises an internal wall, for improving the performance in terms of separation of the two desorbent-free raffinates B2, B3.

Vapour-Phase Isomerization Step C

Advantageously, the process comprises a step C of vapour-phase isomerization of raffinate B2 containing ethylbenzene, ortho-xylene and meta-xylene obtained from the fractionation step B.

Advantageously, the vapour-phase isomerization step allows the isomerization of the OX and of the MX and also of the EB, in a unit operating in the vapour phase, at high temperature and converting the ethylbenzene to xylenes, to treat the EB-rich raffinate B2 obtained from step B.

Preferably, the mass ratio of the raffinate B2 engaged in the isomerization step C to the total raffinate (B2+B3 or B2+B31) obtained on conclusion of step B is between 20% and 90%, preferentially between 25% and 60% and more preferentially between 30% and 45%. Said ratios advantageously make it possible to maximize the production of para-xylene. When said ratio is high, it is possible to increase the production of PX without any trade-off regarding the capacity of the xylene loop; when said ratio is moderate, the production of PX increases more substantially, but is accompanied by a slight increase in the capacity of the xylene loop.

One advantage of the process according to the invention is that of entailing an increase in the stationary concentration of EB in the xylene loop, which allows an increase in the EB conversion by passing into the first vapour-phase isomerization unit.

Thus, the combination of a step of separation by adsorption in an SMB, with a step B of fractionation by distillation in a three-fraction column and of two isomerization steps, makes it possible to improve the overall para-xylene yield of the aromatic loop and to minimize the economic impact.

According to the invention, the vapour-phase isomerization step makes it possible to convert the EB into xylenes with a degree of conversion per ethylbenzene run generally between 10% and 50%, preferably between 20% and 40%, with a loss of C8 aromatics (C8A) of less than 5.0% by weight, preferably less than 3.0% by weight and preferentially less than 1.8% by weight.

The vapour-phase isomerization step is performed at a temperature above 300° C., preferably between 350° and 480° C., a pressure of less than 4.0 MPa, preferably between 0.5 and 2.0 MPa, a space velocity of less than 10.0 $h^{-1}$, preferably between 0.5 $h^{-1}$ and 6.0 $h^{-1}$, a mole ratio of hydrogen to hydrocarbon of less than 10.0, preferably between 3.0 and 6.0, and in the presence of a catalyst including at least one zeolite having channels whose aperture is defined by a ring of 10 or 12 oxygen atoms (10 MR or 12 MR), and at least one metal from group VIII in a content of between 0.1% and 0.3% by weight.

Any catalyst that is capable of isomerizing hydrocarbons containing 8 carbon atoms, which may or may not be zeolite-based, is suitable for the vapour-phase isomerization unit. Preferably, the catalyst used comprises an acidic zeolite, for example of the MFI, MOR, MAZ, FAU and/or EUO structural type. Even more preferably, the catalyst used comprises a zeolite of EUO structural type and at least one metal from group VIII of the Periodic Table of Elements.

According to a preferred variant of the process, the catalyst used in step C comprises from 1% to 70% by weight of a zeolite of EUO structural type, preferably EU-1, comprising silicon and at least one element T preferably chosen from aluminium and boron, the Si/T ratio of which is between 5 and 100.

Preferably, the zeolite is at least partly in hydrogen form, and the sodium content is such that the Na/T atomic ratio is less than 0.1.

Preferably, the catalyst comprises between 0.01% and 2% by weight of tin or indium, and sulfur in a proportion of from 0.5 to 2 atoms per atom of metal from group VIII.

The effluent C1 obtained in step C, having concentrations of PX, OX and MX isomer close to the concentrations at thermodynamic equilibrium is recycled into the simulated moving bed adsorption step A.

In a particular embodiment, when the effluent C1 contains heavy and light compounds formed via undesirable reactions, said effluent is then engaged in an optional fractionation step to remove said compounds.

Liquid-Phase Isomerization Step D

Advantageously, the process comprises a step D of liquid-phase isomerization of fraction B3 or of fraction B31 containing ortho-xylene and meta-xylene obtained from the fractionation step B.

The process according to the invention thus makes it possible to increase the proportion of xylene isomerization performed by the catalyst operating in liquid phase and leading to the lowest losses of C8A.

The xylene isomerization step D is performed in the liquid phase with a degree of EB conversion per run of less than or equal to 5.0%, preferably less than or equal to 3.0%, and preferably less than or equal to 0.2% and allows isomerization of the xylene mixture such that the PX has an approach to thermodynamic equilibrium of greater than or equal to 90.0% and preferentially greater than or equal to 94.0%.

The liquid-phase isomerization step D is performed at a temperature of less than 300° C., preferably between 200 and 260° C., a pressure of less than 4.0 MPa, preferably between 1.0 and 3.0 MPa, a space velocity of less than 5.0 $h^{-1}$ and preferably between 2.0 and 4.0 $h^{-1}$, and in the presence of a catalyst including at least one zeolite having channels whose aperture is defined by a ring of 10 or 12 oxygen atoms (10 MR or 12 MR), preferably a catalyst including at least one zeolite having channels whose aperture is defined by a ring of 10 oxygen atoms (10 MR), and even more preferably a catalyst including a zeolite of ZSM-5 type.

U.S. Pat. No. 8,697,929 describes in greater detail the operating conditions and the vapour-phase and liquid-phase isomerization catalysts that can be used in the process according to the invention.

Advantageously, the effluent D1 obtained in step D, having concentrations of PX, OX and MX isomer close to the concentrations at thermodynamic equilibrium, are recycled into the simulated moving bed adsorption step A.

In a particular embodiment, when the effluent D1 contains heavy and light compounds formed via undesirable reactions, said effluent is then engaged in an optional fractionation step to remove said compounds.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1856050, filed Jun. 29, 2018 are incorporated by reference herein.

EXAMPLES

The examples that follow illustrate the invention without limiting its scope.

Example 1

This example shows the advantage of the invention by comparing the performance of the distillation step B according to the prior art FIG. 2a, the process according to the invention FIGS. 2b and 2c, respectively, in its embodiments denoted ALT0 and ALT1, with references below also to the general process shown in FIG. 1.

This example considers 545 t/h of a C8 fraction (2) obtained from a xylene column and comprising C8 Aromatics (C8A) originating from a reformate, from a transalkylation unit and from one or more isomerization units, its composition being in weight %:

| | |
|---|---|
| C8− | 0.4% |
| EB | 4.1% |
| PX | 23.0% |
| MX | 50.1% |
| OX | 22.3% |
| C9+ | 0.1% |

The C8− fractions correspond to the compounds comprising less than 8 carbon atoms.

Step A of Simulated Moving Bed (SMB) Separation

The C8A fraction is sent to a simulated moving bed adsorption unit A comprising four zones delimited by the injections of feedstocks and of desorbent (B4) and the withdrawals of raffinate (A2) and of extract (A1). The separation step is performed in a simulated bed adsorption unit composed of 15 beds containing barium-exchanged zeolite X, distributed as follows:

3 beds in Zone 1, between the injection of the desorbent B4 and the withdrawal of the extract A1
  6 beds in Zone 2, between the withdrawal of the extract A1 and the injection of the feedstock
  4 beds in Zone 3, between the injection of the feedstock and the withdrawal of the raffinate A2
  2 beds in Zone 4, between the withdrawal of the raffinate A2 and the injection of the desorbent B4

The temperature is 175° C. The desorbent used is para-diethylbenzene, and the desorbent content relative to the feedstock is 1.2 (vol/vol).

Thus implemented, step A of separation by adsorption makes it possible to produce two fractions A1 and A2 feeding the distillation step B:

a fraction A1 containing at least 97.0% of the PX of the feedstock and a portion of the desorbent; said fraction is sent into a distillation step in an extraction column B-C1 so as to recover pure PX at the top (stream B1) and the adsorbent at the bottom (stream B41).
  829 t/h of a raffinate A2 depleted in PX, containing 407 t/h of desorbent.

Figure 2A:
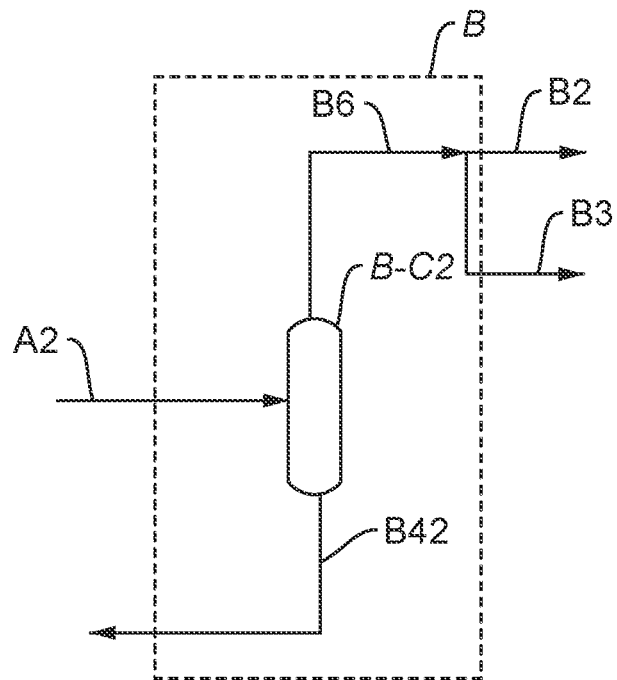
FIG. 2a represents a distillation step B according to the prior art of the raffinate obtained from step A.

Implementation of Step B of Fractionation by Distillation According to the Prior Art (FIG. 2a)

In this embodiment, the raffinate (A2) is fed at theoretical plate 24 into the distillation column (B-C2) containing 47 theoretical plates, a condenser and a reboiler, operating at 0.2 MPa with a reflux ratio of 1.3. Said column makes it possible to produce two streams:

422 t/h of a head raffinate (B6) free of desorbent and
  407 t/h of desorbent (B42) at the bottom, free of C8A, and sent into step A, after a step of heat exchange at the temperature required for the adsorption.

The raffinate (B6) is fractionated into two streams. 90.0% of the raffinate (B6) free of desorbent, denoted (B2), is sent into the first isomerization step (C), and 10% of the residual raffinate (B6) denoted (B3) is fed into the second isomerization step (D).

Said fractionation of the raffinate (A2) by the distillation column requires 86.6 Gcal/h of reboiling energy.

Implementation of Step B of Fractionation by Distillation According to the Invention In a first embodiment (FIG. 2b, ALT0) according to the invention, the raffinate (A2) undergoes a separation step B. Said raffinate is fed at theoretical plate 37 into the three-fraction distillation column (B-C3) containing 60 theoretical plates, a condenser and a reboiler, operating at 0.2 MPa with a reflux ratio of 1.9. Said column makes it possible to produce three streams:
- 367 t/h of a head raffinate (B2) containing 90.0% of ethylbenzene and 87.0% of a mixture consisting of OX and MX contained in the raffinate A2
- 54 t/h of a raffinate (B3) obtained as a side withdrawal on theoretical plate 19, free of desorbent, and
- at the bottom, 407 t/h of desorbent (B42) free of C8A, sent into step A, after a step of heat exchange at the temperature required for the adsorption.

Said fractionation of the raffinate A2 by the three-fraction distillation column requires 86 Gcal/h of reboiling energy.

In a second preferred embodiment (FIG. 2c, ALT1) according to the invention, the raffinate (A2) undergoes a separation step B. Said raffinate is fed at theoretical plate 22 into the three-fraction distillation column (B-C3) containing 47 theoretical plates, a condenser and a reboiler, operating at 0.2 MPa with a reflux ratio of 1.47. This column makes it possible to produce three streams:
- 348 t/h of a head raffinate (B2) containing 90.0% of ethylbenzene contained in the total raffinate (B2+B31) and 82.0% of xylenes contained in the total raffinate (B2+B31)
- 202 t/h of a raffinate (B3) obtained as a side withdrawal on theoretical plate 30 and
- at the bottom, 278 t/h of desorbent (B42) free of C8A, sent into step A, after a step of heat exchange at the temperature required for the adsorption.

The raffinate (B3) containing the desorbent is sent to plate 22 of the second distillation column (B-C4) containing 47 theoretical plates, a condenser and a reboiler, operating at 0.2 MPa and with a reflux ratio of 2.1%, which makes it possible to recover at the top 73 t/h of a raffinate B31 consisting of MX, OX, depleted in PX and with an EB content of 3.0% by weight and finally 129 t/h of a bottom product (B43) containing desorbent free of C8A, which is sent into step A, after a step of heat exchange at the temperature required for the adsorption. The raffinate B31 is sent into the isomerization step D operating in the liquid phase. The fractionation of the raffinate via this implementation ALT1 requires 86.1 Gcal/h of reboiling energy.

On conclusion of the step of fractionation of the raffinate A2 in these various embodiments according to the invention, the EB-rich raffinate B2 is sent into the isomerization step C, and the raffinate B31 is sent into the isomerization step D.

Figure 2B:
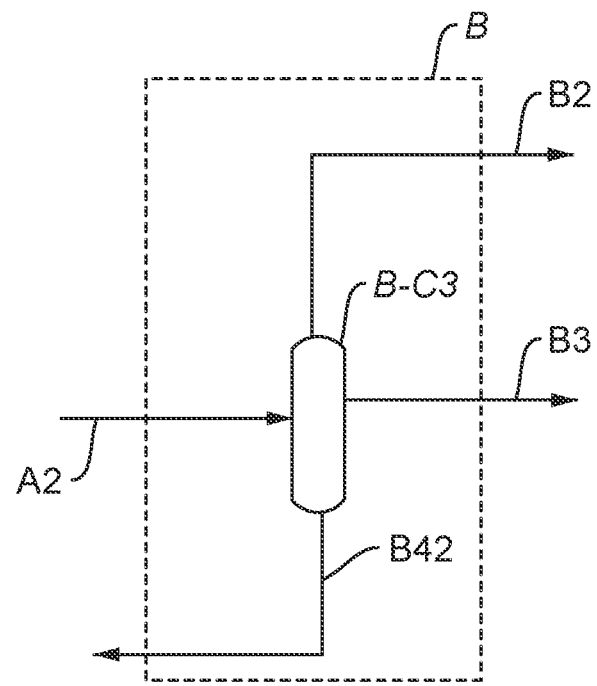
FIG. 2b is a first variant, according to the invention, of step B of distillation of the raffinate obtained from step A.
Figure 2C:
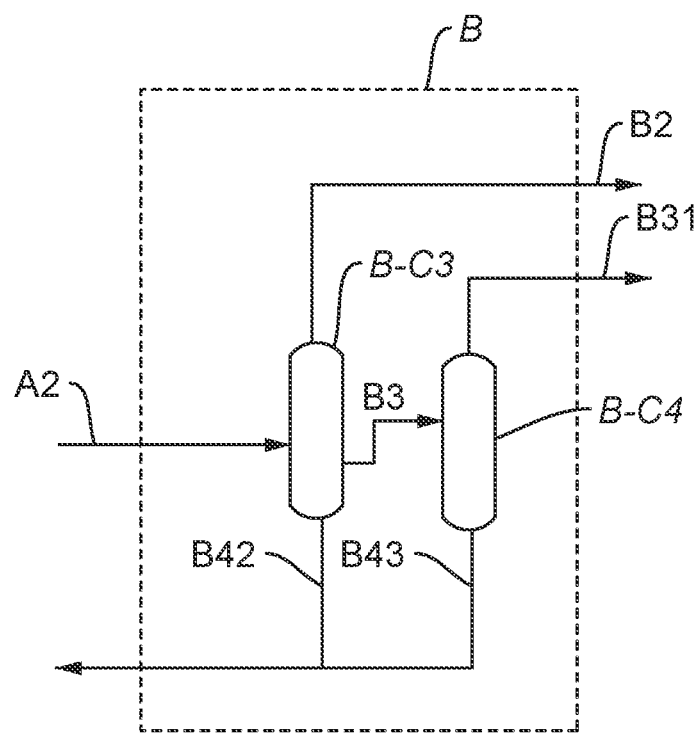
FIG. 2c is a second variant, according to the invention, of step B of distillation of the raffinate obtained from step A.

The performance of the raffinate separation step according to the prior art FIG. 2a, or according to the invention FIG. 2b and FIG. 2c, is summarized below:

|  | Prior art FIG. 2a) | According to the invention ALT0 FIG. 2b) | According to the invention ALT1 FIG. 2c) |
|---|---|---|---|
| DR(EB) | 90.0% | 90.0% | 90.0% |
| DR(XYL) | 90.0% | 87.0% | 82.2% |
| Total Qreb (Gcal/h) | 86.6 | 86.0 | 86.1 |
| Plate No. Col B-C2 | 47 | — | — |
| Plate No. Col B-C3 (3 fractions) | — | 60 | 47 |
| Plate No. Col B-C4 | — | — | 47 |

This example illustrates the advantage of the invention when the adsorption step produces a raffinate. It makes it possible, for the same degree of EB recovery of 90.0% in the raffinate B2, to reduce by 3 points or by 8 points the associated degree of xylene recovery according to the implementation of the invention. Relative to the prior art, in which the degrees of recovery are identical, this enrichment makes it possible to increase the proportion of the raffinate feeding the liquid-phase isomerization unit having moderate losses of C8A and to reduce the proportion feeding the gas-phase isomerization unit having higher losses of C8A. Thereafter, the PX yield of the aromatic complex increases as illustrated in Example 3.

This enrichment requires the use of at least one first three-fraction distillation column, without any impact on the energy required for the reboiling of the fractionation step B, or on the configuration or operation of the adsorption step A.

Relative to the prior art, it is possible to increase the PX yield of the aromatic complex, as illustrated in Example 3.

Example 2

This example shows the advantage of the invention by comparing the performance of the distillation step B according to the prior art (FIG. 3a)), with the process according to the invention (FIG. 3b)), in an embodiment named ALT2.

Step A of Simulated Moving Bed (SMB) Separation

This example considers 545 t/h of a C8 fraction (2) obtained from a xylene column and comprising C8 Aromatics originating from a reformate, from a transalkylation unit and from one or more isomerization units. The composition of said fraction is given in weight percentages:

| C8− | 0.4% |
|---|---|
| EB | 4.1% |
| PX | 23.0% |
| MX | 50.1% |
| OX | 22.3% |
| C9+ | 0.1% |

The C8− fractions correspond to the compounds comprising less than 8 carbon atoms.

This C8A fraction is sent to a simulated moving bed adsorption unit A comprising five zones delimited by the injections of feedstocks and of desorbent (B4) and the withdrawals of raffinates (A21, A22) and of extract (A1). Said simulated bed adsorption unit is composed of 18 beds containing barium-exchanged zeolite X, distributed as follows:
- 3 beds in Zone 1, between the injection of the desorbent (B4) and the withdrawal of the extract (A1)
- 6 beds in Zone 2, between the withdrawal of the extract (A1) and the injection of the feedstock
- 4 beds in Zone 3A, between the injection of the feedstock and the withdrawal of the raffinate (A2)
- 3 beds in Zone 3B, between the withdrawal of the raffinate (A2) and the withdrawal of the raffinate (A22)
- 2 beds in Zone 4, between the withdrawal of the raffinate (A22) and the injection of the desorbent (B4).

The temperature is 175° C., the desorbent used is para-diethylbenzene, and the desorbent content relative to the feedstock is 1.2 (vol/vol).

Thus, the implementation of an SMB separation step A makes it possible to obtain three streams denoted (A1), (A2) and (A22) feeding the distillation step B. The three streams have the following characteristics:

an extract (A1) containing at least 97.0% of the para-xylene PX of the feedstock and a portion of the desorbent, which is sent into an extraction column so as to recover pure PX at the top and the desorbent at the bottom 508 t/h of a first raffinate (A2) depleted in PX, rich in ethylbenzene, containing 98.0% of ethylbenzene EB contained in the total raffinate B2+B31 and 78.0% of the xylenes contained in the total raffinate B2+B31

320 t/h of a second raffinate (A22) depleted in PX, which essentially contains a mixture of MX and OX, the EB content in fraction A8 of which is 0.5%, and another portion of the desorbent.

Implementation of Step B of Fractionation by Distillation According to the Prior Art (FIG. 3a)

In this embodiment, the first raffinate (A2) containing desorbent is fed at theoretical plate 27 into the distillation column (B-C2) containing 47 theoretical plates, a condenser and a reboiler, operating at 0.2 MPa with a reflux ratio of 1.1. The first raffinate without desorbent (B2) is recovered at the top and is sent into the first isomerization step operating in the vapour phase. The second raffinate containing desorbent (A22) is engaged in a separation step B. Said raffinate is fed at theoretical plate 21 into column (B-C4) containing 47 theoretical plates, a condenser and a reboiler, operating at 0.2 MPa with a reflux ratio of 2.7. The second raffinate without desorbent (B3) is recovered in the distillate and is sent into the isomerization step D operating in the liquid phase. The two streams of desorbent B42 and B43 free of C8A, obtained from the bottom of the two raffinate columns (B-C2 and B-C4), are mixed and sent into the simulated moving bed separation step, after a step of heat exchange at the temperature required for the adsorption.

Step B of fractionation of the two raffinates (A2) and (A22) produced by the simulated moving bed require 81.2 Gcal/h of reboiling energy.

Implementation of Step B of Fractionation by Distillation According to the Invention (FIG. 3b, ALT2)

In one embodiment (ALT2) according to the invention, the first raffinate (A2) containing desorbent is fed at theoretical plate 20 into the three-fraction distillation column (B-C3) containing 47 theoretical plates, a condenser and a reboiler, operating at 0.2 MPa with a reflux ratio of 1.38. Said column makes it possible to produce three streams:

284 t/h of a first head raffinate (B2) containing 90.1% of the ethylbenzene content of the total raffinate B2+B31, 73.6 t/h of a second fraction (B3) withdrawn in the liquid phase from theoretical plates 27, containing the residual ethylbenzene and 12% of the xylenes of the total raffinate B2+B31 with desorbent, and 150.6 t/h of a bottom product B42 containing desorbent, free of C8A compounds.

The raffinate (B3) containing desorbent is introduced at plate 18 into a second distillation column (B-C4) containing 47 theoretical plates, a condenser and a reboiler, operating at 0.2 MPa with a reflux ratio of 2.1.

The second raffinate (A22) obtained from the simulated moving bed separation step A is engaged in the distillation step B. Said raffinate (A22) is introduced at plate 24 of this distillation column (B-C4). 137 t/h of a raffinate (B31) are recovered at the top. Said raffinate (B31) is free of desorbent and consists of MX, OX, is depleted in PX and has an EB content of 1.6% by weight. The raffinate (B3) is sent into the isomerization step D operating in the liquid phase. The two streams of desorbent B42 and B43 obtained from the two raffinate columns (B-C3 and B-C4) are mixed and sent to the simulated moving bed, after heat exchange at the temperature required for the adsorption.

The fractionation of the two raffinates (A2) and (A22) requires 84.5 Gcal/h of reboiling energy.

The performance of the raffinate separation step B according to the prior art (FIG. 3a), or according to the invention (FIG. 3b), is summarized below:

|  | Prior art FIG. 3a) | Invention ALT2 FIG. 3b) |
|---|---|---|
| DR(EB) | 98.0% | 90.2% |
| DR(XYL) | 78.0% | 66.1% |
| Total Qreb (Gcal/h) | 81.2 | 84.5 |
| Plate No. raff. Col B-C2 | 47 | — |
| Plate No. raff. Col B-C3 (3 fractions) | — | 47 |
| Plate No. raff. Col2 B-C4 | 47 | 47 |

This example illustrates the advantage of the invention when the adsorption step A produces two raffinates. It makes it possible to achieve, by coupling a distillation step and an adsorption step, better EB/XYL separation than the separation described in the prior art, without, however, having an impact on the amount of equipment or the energy required for reboiling.

The separation step B according to the invention requires the use of a first three-fraction distillation column coupled to a second distillation column.

Relative to the prior art, it is possible to increase the PX yield of the aromatic complex, as illustrated in Example 4.

Example 3

This example shows the advantage of the invention by detailing the performance of a xylene loop represented in FIG. 1 comprising an adsorption step A producing only one raffinate A2,
a step B of fractionation of the raffinate, and
two isomerization steps C and D.

To fully understand the advantage of the invention, the separation step B is performed according to the prior art, or according to the invention in the versions ALT0 and ALT1 as described in Example 1.

The degree of EB recovery, denoted DR(EB), is set at 90.0% and the degrees of xylene recovery, denoted DR(XYL) range between 90.0%, 87.0% and 82.0%.

Said xylene loop is fed with a flow rate of 100 t/h of a C8+ fraction (stream 1, FIG. 1) originating from a reformate containing 68 t/h of C8A fraction, the mass composition of which is given below:

| EB | 16.7% |
|---|---|
| PX | 18.0% |
| MX | 41.0% |
| OX | 24.3% |

Said fraction C8A (stream 1, FIG. 1) is introduced, with the recyclings of the effluents (C1, D1) from the two isomerization steps C and D, at theoretical plate 15 into the xylene column containing 72 plates, operated with a reflux ratio of 1.8, making it possible to recover at the top (stream 2, FIG. 1) 99.8% of the C8A in the distillate and to remove the C9+ from the feedstock (stream 4, FIG. 1) of the simulated moving bed separation unit PX.

Said fraction C8A is engaged in a simulated moving bed separation step A producing an extract A1 rich in PX and in desorbent and a raffinate A2 depleted in PX and containing desorbent. The extract A1 and the raffinate A2 are sent into a fractionation step B as described in Example 1, including several distillation columns. It makes it possible to recycle the desorbent into the adsorption step A, and to produce PX with a purity of 99.8%, and two raffinates, one enriched in EB (B2) and the other depleted in EB (B3 or B31) as described in Example 1 and illustrated in FIGS. 2a, 2b, 2c.

The raffinate (B2), mixed with a recycling of hydrogen, is fed into the ethylbenzene conversion unit in the first isomerization step C, working under the following conditions: pressure: 0.9 MPa, temperature: 376° C., ratio $H_2/HC=4.1$, catalyst: contains platinum and EU-1 zeolite, space velocity: 5 $h^{-1}$.

Under these conditions, the EB conversion is 28.9% (prior art); 29.3% (according to the invention, ALT0 version); 29.9% (according to the invention, ALT1 version), the C8A losses are 1.8% by weight and the approach to equilibrium of PX is 92.0% and of OX is 87.0%.

At the reactor outlet, a separation train makes it possible to produce a gas dominantly containing hydrogen, toluene and a paraffinic and naphthenic fraction sent to the reactor inlet. The heaviest part of the effluent (C1) is recycled into the inlet of the xylene column (FIG. 1).

The raffinate (B3) is fed into the xylene isomerization unit in the second isomerization step D, working under the following conditions: temperature 240° C., pressure 1.8 MPa, space velocity 2.5 $h^{-1}$, with a catalyst containing a zeolite of ZSM-5 type.

Under these conditions, the EB conversion is 3.4% and the approach to equilibrium of the PX is 94.5%.

The effluent from the reaction section (D1) is recycled into the xylene column (FIG. 1).

The material balance for the xylene loop thus described is summarized in the table below:

| | Prior art 1 | Invention ALT0 | Invention ALT1 |
|---|---|---|---|
| Number of isomerization units | 2 | 2 | 2 |
| Number of effluents in the adsorption unit | 2 | 2 | 2 |
| Fractionation of the raffinate with a distillation column | 2 fractions | 3 fractions | 3 fractions + 1 side column |
| Performance of fractionation step B | | | |
| DR(EB) | 0.90 | 0.90 | 0.90 |
| DR(XYL) | 0.90 | 0.87 | 0.82 |
| Capacity of the units (kta) | | | |
| Step A | 2917 | 2912 | 2904 |
| Step C | 2142 | 2080 | 1981 |
| Step D | 237 | 294 | 383 |
| Total flow rate of raffinate without desorbent | 2379 | 2373 | 2364 |
| Fraction of the raffinate fed into the first isomerization step (C) | 90.0% | 87.6% | 83.8% |
| Sieves and catalysts (t) | | | |
| Amount of adsorption sieves (Step A) | 476.0 | 475.7 | 475.2 |
| Amount of catalyst (Step C) | 51 | 50 | 47 |
| Amount of catalyst (Step D) | 11 | 14 | 18 |
| Production | | | |
| PX produced (kt/y) | 527.7 | 528.5 | 529.9 |
| Delta Gain produced (MM$/y) | 0 | 1.27 | 3.29 |

This example illustrates the advantage of the invention, which makes it possible to increase the productivity of a xylene loop containing two isomerizations, with a simulated moving bed producing two effluents using a first three-fraction distillation column in the fractionation step B.

The energy consumption of the fractionation step B is not affected. The gain in PX production, estimated on the basis of a mean PX price of 1500$/t ($/tonne), is 1.3 MM$/y (millions of dollars/year) for the version ALT0 and 3.3 MM$/y for the version ALT1 and justify the marginal investment associated with the modifications of the fractionation step B.

Example 4

This example shows the advantage of the invention by detailing the performance of a xylene loop shown in FIG. 1 comprising an adsorption step A producing two raffinates A2 and A22, a raffinate fractionation step B, and two isomerization steps C and D. To illustrate the advantage of the invention, the separation step B is performed according to the prior art, or according to the version ALT2 described in Example 2. Thus, the degrees of recovery of EB DR(EB), and of xylenes DR(XYL), obtained via the process according to the prior art are, respectively, 98.0% and 78.0%, whereas, according to the version ALT2 of the process according to the invention, the degrees of recovery are, respectively, 90.0% and 66%.

The xylene loop is fed with 100 t/h of a C8+ fraction (stream 1, FIG. 1) originating from a reformate containing 68 t/h of C8A fraction, the mass composition of which is given below:

| | |
|---|---|
| EB | 16.7% |
| PX | 18.0% |
| MX | 41.0% |
| OX | 24.3% |

Said fraction C8A (stream 1, FIG. 1) is introduced, with the recyclings of the effluents from the two isomerization steps, at theoretical plate 15 into the xylene column containing 72 plates, operated with a reflux ratio of 1.8, making it possible to recover at the top (stream 2, FIG. 1) 99.8% of the C8 Aromatics in the distillate and to remove the C9+ from the feedstock (stream 4, FIG. 1) of the simulated moving bed separation unit PX. Said fraction C8A is fed into a simulated moving bed producing an extract A1 rich in PX and in desorbent and two raffinates A2 and A22 depleted in PX and containing desorbent.

The extract and the raffinate are sent into a separation step B, described in Example 1, including several fractionation columns. The desorbent (B4) thus separated out is recycled into the adsorption step A. Said step B makes it possible to produce para-xylene with a purity of 99.8%, and two raffinates enriched in EB (B2) or depleted in EB (B3 or B31) as described in Example 2 and illustrated in FIGS. 3a and 3b.

The raffinate B2, mixed with a recycling of hydrogen, is fed into the ethylbenzene conversion unit in the first isomerization step C, working under the following conditions: pressure: 0.9 MPa, temperature: 376° C., ratio H2/HC=4:1, catalyst: contains platinum and EU-1 zeolite, space velocity: 5 $h^{-1}$.

Under these conditions, the EB conversion is 30.6% (prior art); 32.1% (invention, ALT2 version), the C8A losses are 1.8% by weight and the approach to equilibrium of PX is 92% and of OX is 87%.

At the reactor outlet, a separation train makes it possible to produce a gas dominantly containing hydrogen C2, toluene and a paraffinic and naphthenic fraction sent to the reactor inlet. The heaviest part of the isomerate (C1) is recycled into the inlet of the xylene column.

The raffinate B3 is fed into the xylene isomerization unit in the second isomerization step D, working under the following conditions: temperature 240° C., pressure 1.8 MPa, space velocity 2.5 $h^{-1}$, with a catalyst containing zeolite of ZSM-5 type.

Under these conditions, the EB conversion is 3.4 and the approach to equilibrium of the PX is 94.5%.

The effluent from the reaction section (D1) is recycled into the xylene column.

The material balance for the xylene loop is summarized in the table below:

|  | Prior art 2 | Invention ALT2 |
|---|---|---|
| Number of isomerization units | 2 | 2 |
| Number of effluents in the adsorption unit | 3 | 3 |
| Fractionation of the raffinate | by adsorption + 2 raffinate columns | by adsorption + 1 3-fraction raffinate column + 1 side column |
| Performance of fractionation step B | | |
| DR(EB) | 0.98 | 0.90 |
| DR(XYL) | 0.78 | 0.66 |
| Capacity of the units (kta) | | |
| Step A | 2866 | 2878 |
| Step C | 1897 | 1662 |
| Step D | 428 | 672 |
| Total flow rate of raffinate without desorbent | 2325 | 2334 |
| Fraction of the raffinate fed into the first isomerization step C | 81.6% | 71.2% |
| Sieves and catalysts (t) | | |
| Amount of adsorption sieves (Step A) | 565.1 | 567.8 |
| Amount of catalyst (Step C) | 45 | 40 |
| Amount of catalyst (Step D) | 20 | 32 |
| Production | | |
| PX produced (kt/y) | 531.9 | 534.2 |
| Delta Gain produced (MM$/y) | 0 | 3.4 |

These results clearly illustrate that the process according to the invention makes it possible to increase the para-xylene yield of a xylene loop by implementing a simulated moving bed producing three effluents, using a first three-fraction distillation column in the separation step B as described in Example 1. Advantageously, this particular implementation of the process according to the invention does not have an impact on the amount of equipment or the energy expenditure.

The estimated gain based on a mean PX cost of 1500$/t is 3.4 MM$/y.

Example 5

In a particular version named ALT3, the process is performed with the same equipment and in the same configuration of the xylene loop as for the version ALT2 of Example 4 (FIG. 3b). This example illustrates the advantage of the invention when it is desired to obtain very high yields of PX, from the same feedstock, with a marginal increase in isomerization catalyst and sieves.

The operating parameters of the adsorption step A are identical to those of Example 4, but the operating parameters of the raffinate fractionation step B are modified so that the flow rate of EB-rich raffinate B2 from the first distillation column B-C3 is reduced to the benefit of the side withdrawal B3 feeding the second distillation column B-C4 and also its resulting flow rate of distillate (B31).

In this embodiment, the new performance qualities of the fractionation step B are such that DR(EB)=60% and DR(XYL)=38%. Said raffinate B2 is then engaged in the isomerization step C. This implementation makes it possible to increase the proportion of xylene isomerization by the catalyst having the least losses of C8A, and finally to increase the yield of PX.

Since the EB conversion per run in the isomerization step D is low, the degree of EB recycling increases, which has the effect of increasing its stationary concentration. Thereafter, the EB conversion per run in the first vapour-phase isomerization, governed by a thermodynamic equilibrium, is also increased and reaches 36.5%.

Advantageously, the combination of the two isomerization steps according to the invention makes it possible to achieve high PX production, with low trade-offs in terms of increase in capacity.

The material balance for the xylene loop thus described is summarized in the table below:

|  | Prior art 2 | Invention ALT3 |
|---|---|---|
| Number of isomerization units | 2 | 2 |
| Number of effluents in the adsorption unit | 3 | 3 |
| Fractionation of the raffinate | by adsorption + 2 raffinate columns | by adsorption + 1 3-fraction raffinate column + 1 side column |
| Performance of fractionation step B | | |
| DR(EB) | 0.98 | 0.60 |
| DR(XYL) | 0.78 | 0.38 |
| Capacity of the units (kta) | | |
| Step A | 2866 | 2969 |
| Step C | 1897 | 1063 |
| Step D | 428 | 1357 |
| Total flow rate of raffinate without desorbent | 2325 | 2419 |
| Fraction of the raffinate fed into the first isomerization step C | 81.6% | 43.9% |
| Sieves and catalysts (t) | | |
| Amount of adsorption sieves (Step A) | 565.1 | 586 |
| Amount of catalyst (Step C) | 45 | 25 |
| Amount of catalyst (Step D) | 20 | 64 |
| Production | | |
| PX produced (kt/y) | 531.9 | 537.9 |
| Delta Gain produced (MM$/y) | .0 | 9.0 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for producing para-xylene from a feedstock containing xylenes and ethylbenzene, comprising:
a step A of separating said feedstock in a simulated moving bed in the presence of a desorbent and a zeolite adsorbent into a first fraction containing para-xylene and desorbent and a second fraction containing ethylbenzene (EB), ortho-xylene OX), meta-xylene (MX), and desorbent,
wherein the separating is performed at a temperature of between 20 and 250° C., at a pressure of between 1.0 and 2.2 MPa, and with a volume ratio of the desorbent to the feedstock of between 0.4 and 2.5, and
a step B of fractionating the second fraction in a first distillation column to produce a first stream containing EB, OX and MX, a second stream containing OX, MX and desorbent, and a third stream containing desorbent, and fractionating the second stream in a second distillation column to produce a fourth stream containing MX and OX, free of desorbent, and a fifth stream consisting of desorbent.

2. The process according to claim 1, wherein the first stream has an EB content greater than the EB content of the second stream.

3. The process according to claim 2, wherein the EB content of the first stream is at least 1.0% greater than that of the second stream.

4. The process according to claim 1, wherein the first distillation column comprises between 30 and 80 theoretical plates.

5. The process according to claim 1, wherein step A further comprises separating a third fraction depleted in EB and containing a mixture of MX, OX and desorbent.

6. The process according to claim 5, wherein the third fraction is introduced into the second distillation column.

7. The process according to claim 6, wherein the third fraction is introduced into the second distillation column below a lateral point of injection of the second stream.

8. The process according claim 1, wherein the first distillation column is a column comprising an internal wall.

9. The process according to claim 1, further comprising a step C of vapour-phase isomerization of the first stream.

10. The process according to claim 1, comprising a step D of liquid-phase isomerization of the fourth stream.

11. The process according to claim 9, wherein step C is performed at a temperature above 300° C., a pressure of less than 4.0 MPa, a space velocity of less than 10.0 $h^{-1}$, a mole ratio of hydrogen to hydrocarbon of less than 10.0, and in the presence of a catalyst including at least one zeolite having channels whose aperture is defined by a ring of 10 or 12 oxygen atoms, and at least one metal from group VIII in a content of between 0.1% and 0.3% by weight.

12. The process according to claim 11, wherein the catalyst comprises from 1% to 70% by weight of an EUO zeolite comprising silicon and at least one element T chosen from aluminium and boron, wherein a Si/T ratio is between 5 and 100.

13. The process according to claim 10, wherein step D is performed at a temperature of less than 300° C., a pressure of less than 4.0 MPa, a space velocity of less than 5.0 $h^{-1}$, and in the presence of a catalyst including at least one zeolite having channels whose aperture is defined by a ring of 10 or 12 oxygen atoms.

* * * * *